(12) United States Patent
Chan

(10) Patent No.: US 6,516,977 B2
(45) Date of Patent: Feb. 11, 2003

(54) SYSTEM AND METHOD FOR MIXING BONE CEMENT

(76) Inventor: Kwan-Ho Chan, 4803 1st Pl., Lubbock, TX (US) 79416

(*) Notice: Subject to any disclaimer, the term of this patent is extended or adjusted under 35 U.S.C. 154(b) by 0 days.

(21) Appl. No.: 09/928,674

(22) Filed: Aug. 13, 2001

(65) Prior Publication Data
US 2002/0043542 A1 Apr. 18, 2002

Related U.S. Application Data

(60) Continuation of application No. 09/115,089, filed on Jul. 14, 1998, now abandoned, which is a division of application No. 08/604,194, filed on Feb. 21, 1996, now Pat. No. 5,779,356.

(51) Int. Cl.⁷ .............................. B01F 13/06
(52) U.S. Cl. .................... 222/394; 222/325; 222/398; 222/541.6; 215/49; 422/100; 422/102
(58) Field of Search .................. 222/394, 398, 222/325, 541.6; 215/47, 49; 422/100, 102

(56) References Cited

U.S. PATENT DOCUMENTS

| | | | |
|---|---|---|---|
| 1,680,616 A | 8/1928 | Horst | |
| 2,679,140 A | 5/1954 | Burchett | |
| 3,244,331 A | 4/1966 | Kharasch | |
| 3,892,237 A | * 7/1975 | Steiner | 128/216 |
| 4,185,072 A | 1/1980 | Puderbaugh et al. | |
| 4,208,133 A | 6/1980 | Korte-Jungermann | |
| 4,361,253 A | * 11/1982 | Flynn et al. | 222/162 |
| 4,506,793 A | * 3/1985 | MacGregor et al. | 215/32 |
| 4,721,390 A | 1/1988 | Lidgren | |
| 4,758,096 A | 7/1988 | Gunnarsson | |
| 4,799,801 A | 1/1989 | Bruning | |
| 4,973,168 A | * 11/1990 | Chan | 366/139 |
| 5,252,301 A | 10/1993 | Nilson et al. | |
| 5,306,277 A | 4/1994 | Bryant et al. | |
| 5,328,262 A | 7/1994 | Lidgren et al. | |
| 5,435,645 A | 7/1995 | Faccioli et al. | |
| 5,545,460 A | 8/1996 | Tanaka et al. | |
| 5,551,778 A | 9/1996 | Hauke et al. | |
| 5,586,821 A | * 12/1996 | Bonitati et al. | 366/139 |

FOREIGN PATENT DOCUMENTS

| EP | 0603871 A3 | 12/1993 |
|---|---|---|
| EP | 0603871 A2 | 12/1993 |

* cited by examiner

Primary Examiner—J. Casimer Jacyna
(74) Attorney, Agent, or Firm—Pandiscio & Pandiscio, P.C.

(57) ABSTRACT

An apparatus for mixing bone cement in a vacuum includes a container for mixing first and second components of a bone cement in a vacuum, the container having a sealed body defining an interior space and a selected quantity of the first component disposed in the interior space. The container is provided with an injection port for admitting the second component into the interior space vacuum source. A mixing paddle is disposed in the interior space and connected to a handle therefor extending out of the container. A plurality of indirect pathways extend between the interior space and the exhaust port which permit gas to pass therethrough out of the interior space, but prevent the bone cement first and second components from passing therethrough.

1 Claim, 10 Drawing Sheets

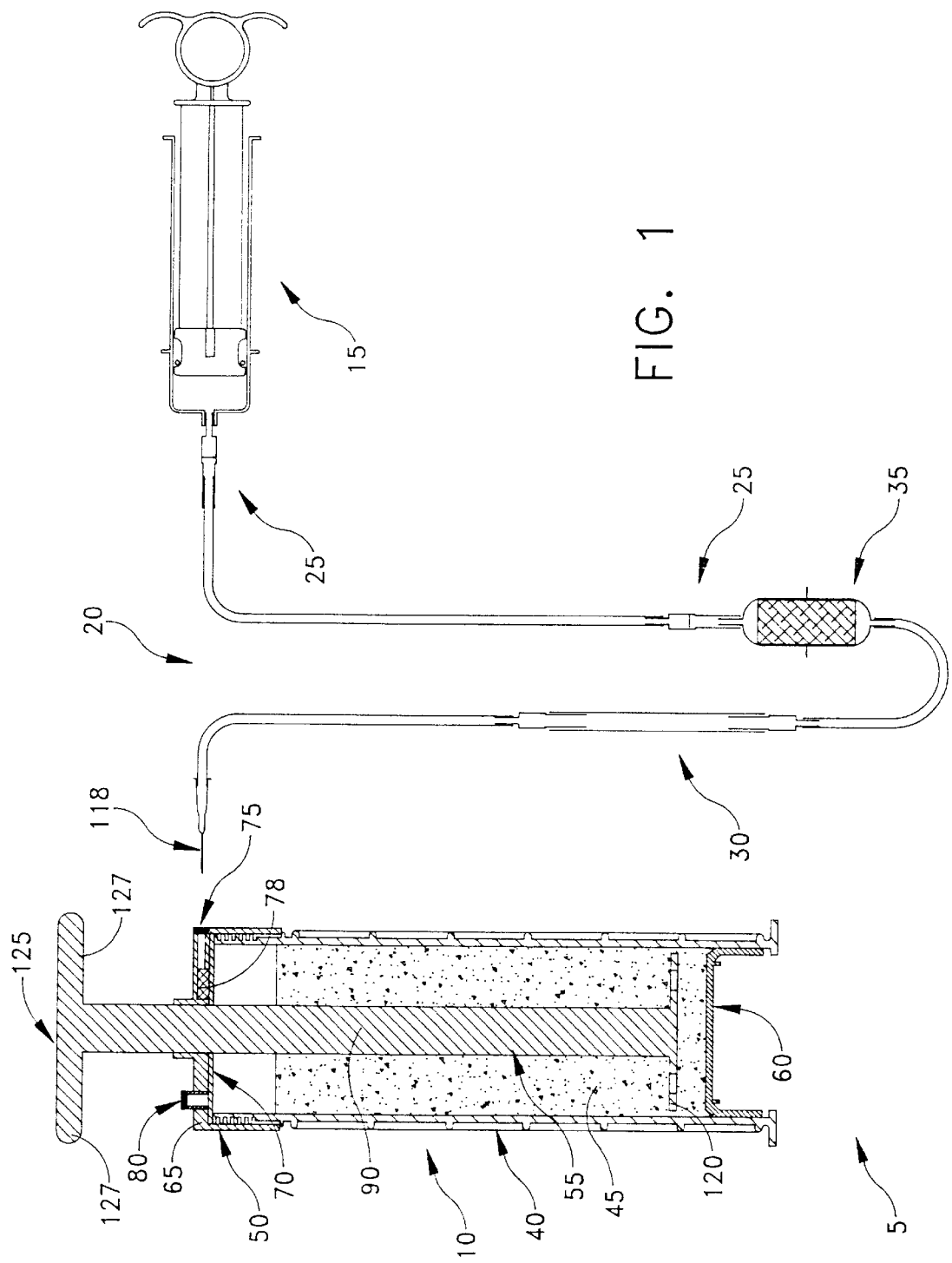

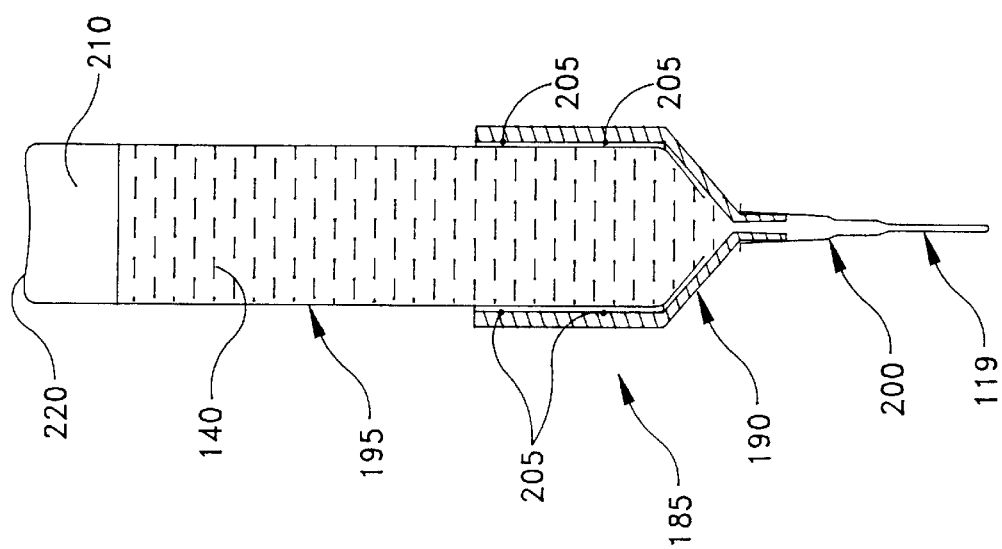
FIG. 9
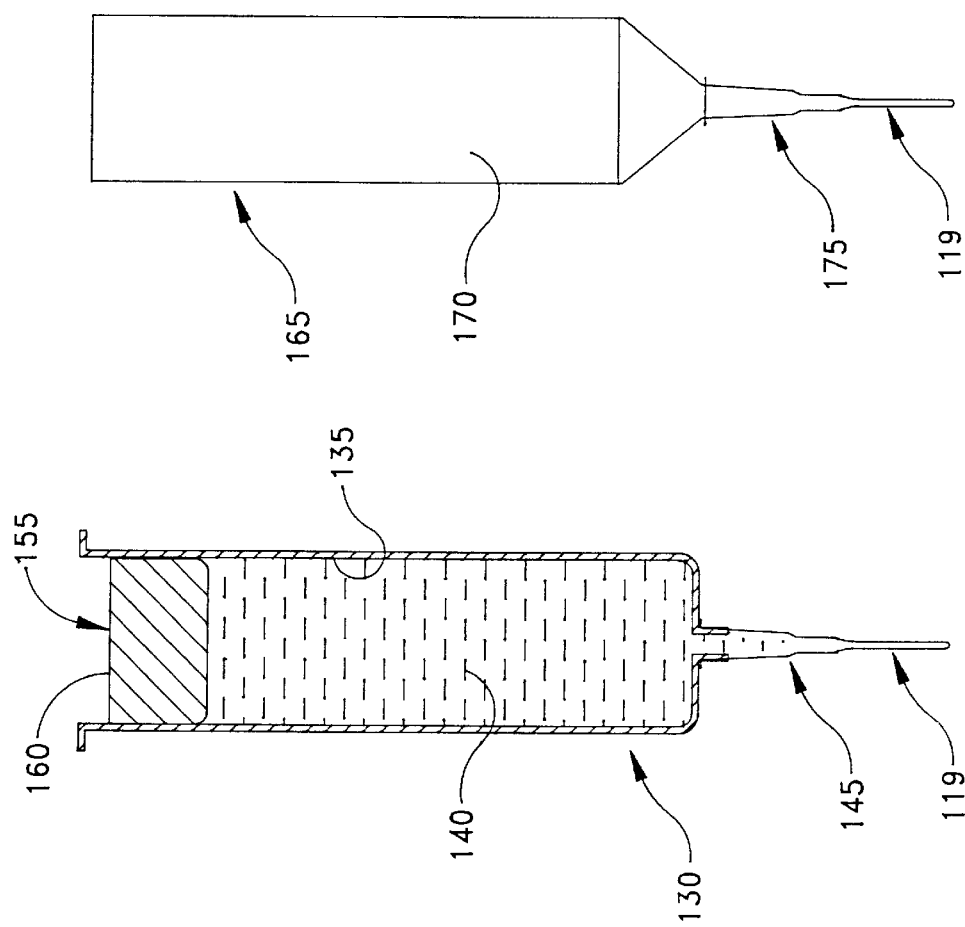
FIG. 8
FIG. 7

SYSTEM AND METHOD FOR MIXING BONE CEMENT

This application is a continuation of U.S. patent application Ser. No. 09/115,089, filed Jul. 14, 1998, by Kwan-Ho Chan for SYSTEM AND METHOD FOR MIXING BONE CEMENT, now abandoned, which is a division of U.S. patent application Ser. No. 08/604,194, filed Feb. 21, 1996, by Kwan-Ho Chan for SYSTEM AND METHOD FOR MIXING BONE CEMENT, now U.S. Pat. No. 5,779,356.

FIELD OF THE INVENTION

This invention relates to bone cements in general, and more particularly to systems and methods for preparing bone cements from a solid component and a liquid component by mixing the two components in a vacuum.

BACKGROUND OF THE INVENTION

In many orthopaedic surgical procedures, bone cements are used to fix implants to bone. These bone cements are generally polymeric and/or copolymeric materials which are prepared by polymerizing the cement's constituent components as the cement is needed during the surgical procedure. More particularly, such bone cements are typically prepared by polymerizing a liquid monomer and a powdered polymer and/or copolymer, e.g. polymethyl methacrylate ("PMMA") and/or a polystyrene copolymer.

Unfortunately, it has been found that as the cement's constituent components are mixed together to effect the aforementioned polymerization, air bubbles are generally introduced into the cement. The presence of these air bubbles increases the porosity of the cement and thereby undermines its structural integrity. Conversely, it has also been found that the strength of the cement can be significantly increased if the air bubbles are eliminated from the mixture.

On account of the foregoing, bone cements of the sort described above are preferably prepared by mixing the constituent components in a vacuum.

Unfortunately, prior art systems and methods for mixing bone cement in a vacuum in an operating room environment have not proven to be particularly convenient to use. Among other things, such prior art systems and methods generally require operating room personnel to transfer the bone cement's powdered polymer and/or copolymer component into a mixing bowl from its shipping container, and then to transfer the bone cement's liquid monomer component from its shipping container into the same mixing container prior to establishing a vacuum in the mixing bowl and then effecting mixing.

OBJECTS OF THE INVENTION

Accordingly, one object of the present invention is to provide an improved system for mixing bone cement.

And another object of the present invention is to provide more convenient system for mixing bone cement in a vacuum in an operating room environment.

Still another object of the present invention is to provide an improved method for mixing bone cement.

Yet another object of the present invention is to provide more convenient method for mixing bone cement in a vacuum in a operating room environment.

SUMMARY OF THE INVENTION

These and other objects of the present invention are achieved through the provision and use of a novel system and method for mixing bone cement.

The novel system for mixing bone cement generally comprises (i) a container within which the constituent components of the bone cement are mixed under vacuum; (ii) a vacuum pump for pulling a vacuum; (iii) a vacuum line interconnecting the vacuum pump and the container; (iv) a check valve disposed in the vacuum line for maintaining a vacuum pulled in the container by the vacuum pump; (v) a vacuum indicator disposed in the vacuum line for indicating when a predetermined level of vacuum has been attained in the container; and (vi) a filter disposed in the vacuum line for preventing unwanted materials (e.g., powdered polymer and/or copolymer, liquid monomer, and/or mixed cement) from passing from the container to the check valve and/or vacuum pump.

In accordance with the present invention, the bone cement's powdered polymer and/or copolymer component is pre-packaged in the aforementioned container, and the bone cement's liquid monomer component is pre-packaged in a separate holder.

In one form of the invention, the container can comprise a sealed cartridge for a cement dispenser, or a sealed mixing bowl or other vessel. The container comprises an injection port for connection to the holder containing the bone cement's liquid monomer component, an exhaust port for connection to the vacuum line and hence the vacuum pump, and an agitator having a mixing paddle disposed inside the sealed container and an actuating handle disposed outside the sealed container, with a shaft connecting the mixing paddle to the handle. Barrier means are disposed inside the container, between the contents of the container and the exhaust port. These barrier means comprise a plurality of indirect pathways which permit gas to pass out of the container via the exhaust port but prevent solid and/or liquid material from passing out of the container via the exhaust port. Preferably, an absorbent filter is disposed in the exhaust port, downstream from the barrier means but upstream from the vacuum line, to trap any solid and/or liquid material which might pass by the barrier means.

In another form of the invention, the container comprises sealed cartridge for a cement dispenser. This cartridge comprises an exhaust port for connection to the vacuum line and hence the vacuum pump, an agitator having a mixing paddle disposed inside the sealed cartridge and an actuating handle disposed outside the sealed cartridge, with a hollow shaft connecting the mixing paddle to the handle, and an injection port for connection to the holder containing the bone cement's liquid monomer component. In this form of the invention, the injects port is disposed in the handle of the agitator and communicates with the interior of the sealed container through the agitator's hollow handle. A porous plug closes off the distal end of the hollow handle, whereby liquid monomer can pass from the injection port through to the interior of the sealed container but powdered polymer and/or copolymer and/or mixed cement will be prevented from passing out of the sealed container through the agitator during cement mixing. Preferably the agitator's shaft is formed out of a thin-walled exterior tube and a resilient interior tube, with the thin-walled exterior tube including a breakaway notch, and with the distal end of the resilient interior tube being connected to the porous plug, whereby, at the conclusion of cement mixing, the handle of the agitator can be retracted relative to the container, the thin-walled exterior tube can be broken off at the breakaway notch, and the resilient interior tube can be used to withdraw the porous plug from the remaining stub of the thin-walled exterior tube, whereby the stub of the thin-walled exterior tube can become an ejection port for the sealed cartridge.

In still another form of the invention, the container can comprise a sealed cartridge for a cement dispenser, or a sealed mixing bowl or other vessel. In this form of the invention, the holder containing the bone cement's monomer component comprise glass ampoule having an easily fractured neck at one end. The container comprises an injection port for connection (through intervening elements) to the monomer ampoule, an exhaust port connection to the vacuum line and hence the vacuum pump, and an agitator having a mixing paddle disposed inside the sealed container and an actuating handle disposed outside the sealed container, with a shaft connecting the mixing paddle to the handle. The monomer ampoule is disposed in an ampoule breaker/injector device which is connected to the container's injection port. The apparatus is arranged so that when a vacuum is drawn in the sealed container, the monomer ampoule will be automatically broken at its easily fractured neck by forces generated by the vacuum and the liquid monomer will then be draw down into the sealed container through the container's injection port.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein:

FIG. 1 is a schematic view of a system for mixing bone cement;

FIG. 7 is a side view in section of one type of holder for containing the bone cement's liquid monomer component, wherein the holder comprises a syringe;

FIG. 8 is a side view of another type of holder for containing the bone cement's liquid monomer component, wherein the holder comprises a collapsible package;

FIG. 9 is a side view in section of still another type of holder for containing the bone cement's liquid monomer component, wherein the holder comprises an injector sleeve fit over the distal end of a glass ampoule storing the liquid monomer component;

DETAILED DESCRIPTION OF THE PREFERRED EMBODIMENTS

Figure 3:
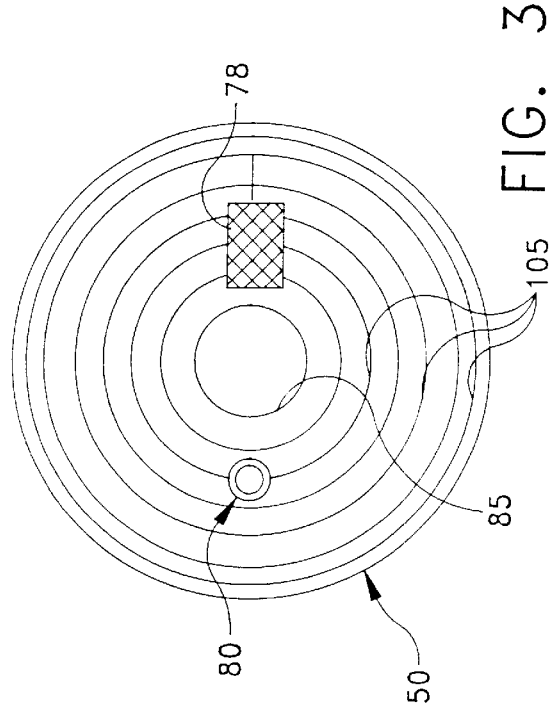
FIG. 3 is a bottom view of the cap portion of the container shown in FIG. 1.

Looking first at FIG. 1, a system 5 for mixing bone cement is shown. System 5 generally comprises a container 10 within which the constituent components of the bone cement are mixed under vacuum, a vacuum pump 15 for pulling a vacuum, a vacuum line 20 interconnecting vacuum pump 15 and container 10, one or more check valves 25 disposed in vacuum line 20 for maintaining a vacuum pulled in container 10, a vacuum indicator 30 disposed in vacuum line 20 for indicating when a predetermined level of vacuum has been attained in container 10, and a filter 35 containing activated charcoal disposed in vacuum line 20 for absorbing unwanted monomer fumes.

In accordance with the present invention, the bone cement's powdered polymer and/or copolymer component is pre-packaged in sealed container 10, and the bone cement's liquid monomer component is pre-packaged in a separate holder.

Still looking now at FIG. 1, container 10 comprises a container body 40 filled with the bone cement's powdered polymer or copolymer component 45, a cap 50 for sealing off container body 40, and an agitator 55 for mixing the bone cement's constituent components within container 10.

For purposes of the present invention, container body 40 can comprise a cartridge for a cement dispenser, in which case container body 40 can be mounted directly in a cement dispenser after the bone cement has been mixed under vacuum. Alternatively, container body 40 can comprise a simple mixing bowl or other vessel, in which case the bone cement is transferred to a cartridge for a cement dispenser after the bone cement has been mixed in container 10. In FIG. 1, container body 40 is shown to be a cartridge for a cement dispenser, and to this end it includes a drive plug 60 which can be urged down the length of container body 40 so as to eject cement from the cartridge, in ways well known in the art.

Looking next at FIGS. 1–5, container cap 50 seals off the distal end of container body 40 so as to form the sealed container 10. Cap 50 includes a cap housing 65, barrier means 70 (FIGS. 1, 4 and 5) disposed on the distal side of cap 50, an exhaust port 75 for connection to vacuum line 20, an absorbent filter 78 disposed in exhaust port 75 for preventing unwanted materials (e.g., powdered polymer or copolymer, liquid monomer, and/or mixed cement) from passing out of container 10 through exhaust port 75, and an injection port 80 for connection to the holder containing the bone cement's liquid monomer component.

Figure 2:
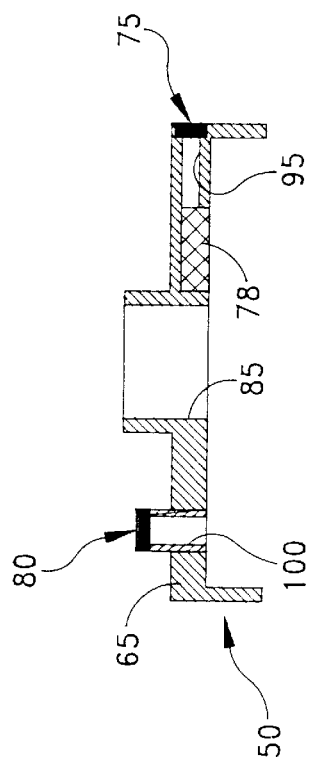
FIG. 2 is a side view in section of the cap portion of the container shown in FIG. 1.

Looking next at FIGS. 2 and 3, cap housing 65 includes an opening 85 to receive the shaft 90 (FIG. 1) of agitator 55. Cap housing 65 also includes an opening 95 which makes up part of exhaust port 75, an opening 100 which makes up part of injectic port 80, and shallow surface grooves 105 (FIG. 3)

which are formed on the underside of cap housing 65. Surface grooves 105 cooperate with barrier means 70 to provide "indirect pathways" between the interior of container 10 and exhaust port 75, as will hereinafter be discussed in further detail.

Figure 5:
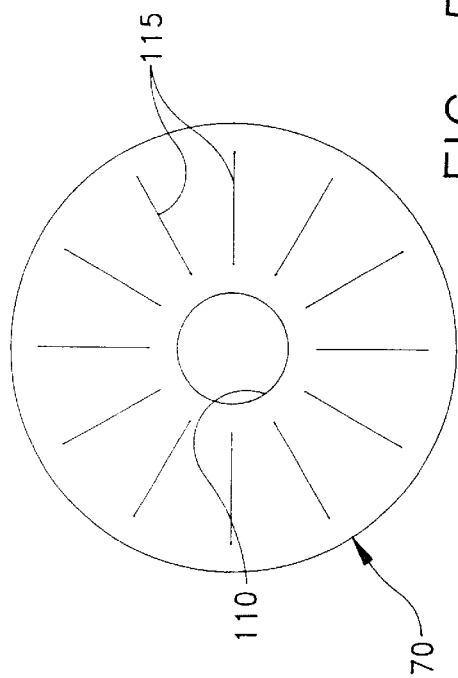
FIG. 5 is a bottom view of the barrier means associated with the container shown in FIG. 1.
Figure 4:
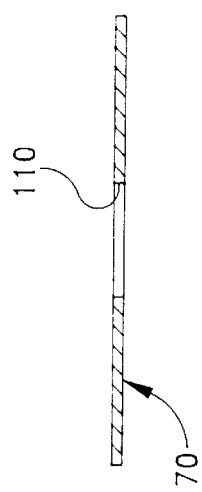
FIG. 4 is a side view in section of the barrier means associated with the container shown in FIG. 1.

Looking next at FIGS. 1, 4 and 5, barrier means 70 are disposed adjacent the distal side of cap housing 65. Barrier means 70 are formed out of a non-porous material such as polyethylene. Barrier means 70 are formed in the shape of a thin disk and includes a central hole 110 and a plurality of radial slits 115 (FIG. 5). Central hole 110 is sized so as to accommodate shaft 90 of agitator 55. Radial slits 115 cooperate with surface grooves 105 of cap housing 65 so as to define a plurality of indirect pathways extending between the interior of container 10 and exhaust port 75. These indirect pathways permit gas to pass out of container 10 via exhaust port 75, whereby the interior of container 10 can be placed into a vacuum condition, but prevent solid and/or liquid material from passing out of container 10 via exhaust port 75. This helps protect the one or more check valves 25 and/or the vacuum pump 15, which elements are located downstream in vacuum line 20. Preferably multiple indirect paths are provided, so that gas evacuation can continue even if one or more paths become blocked with solids and/or liquids.

Exhaust port 75 is a valved connector arrangement which coacts with a counterpart connector arrangement 118 (FIG. 1) disposed on the distal end of vacuum line 20 so as to permit vacuum pump 15 to evacuate air from container 10. Connector arrangement 118, located on the distal end of vacuum line 20, and the counterpart valved connector arrangement of exhaust port 75 located on container 10, may comprise any one of the many connector sets well known in the art. Such connector sets typically utilize a male-female coupling, with the valved connector arrangement of exhaust port 75 including some sort of check valve arrangement so as to render exhaust port 75 self-sealing when it is not being engaged by connector arrangement 118. By way of example, connector arrangement 118 might comprise something equivalent to the blunt inflation pump cannulas of the type commonly used to inflate an ordinary basketball or football, and the valved connector arrangement of exhaust port 75 might comprise something equivalent to the rubber self-sealing inflation ports used on such basketballs and footballs. Alternatively, the counterpart connectors might comprise a Clave™ valve Needleless Connector (ICU Medical Inc., Irvine, Calif.), or an InterLink™ System (Baxter Healthcare Corporation, Deerfield, Ill.) injection port with pre-slit septum in combinatic with an InterLink™ cannula (Becton Dickinson & Co., Franklin Lake, N.J.). For the purposes of the present invention, the principal requirements for connector arrangement 118 and the valved connector arrangement of exhaust port 75 are that (i) they are capable of making an airtight connection when they are in engagement with one another, and (ii) the valved connector arrangement of exhaust port 75 is self-sealing when connector arrangement 118 (and hence the distal end of vacuum line 20) is disconnected from container 10.

Absorbent filter 78 is disposed in exhaust port 75, downstream from barrier means 70 but upstream from vacuum line 20. Absorbent filter 78 serves to remove any material (e,g., powdered polymer and/or copolymer, liquid monomer, and/or mixed cement) that may get past the indirect pathways discussed above. Absorbent filter 78 is preferably made from a cellulose material of the sort well known in the art.

Injection port 80 is a valved connector arrangement which coacts with a counterpart connector arrangement 119 (FIG. 7) disposed on the distal end of a holder containing the bone cement's liquid monomer component so as to permit liquid monomer to be introduced into container 10. Connector arrangement 119, located on the distal end of a holder containing the bone cement's liquid monomer component, and the counterpart valved connector arrangement of injection port 80, located on container 10, may comprise any one of the many connector sets well known in the art. Such connector sets typically utilize a male-female coupling, with the valved connector arrangement of injection port 80 including some sort of check valve arrangement so as to render injection port 80 self-sealing when it is not being engaged by connector arrangement 119. By way of example, connector arrangement 119 might comprise something equivalent to the blur inflation pump cannulas of the type commonly used to inflate an ordinary basketball or football, and the valved connector arrangement of injection port 80 might comprise something equivalent to the rubber self-sealing inflation ports used on such basketballs and footballs. Alternatively, the counterpart connectors might comprise a Clave™ valve Needleless Connector (ICU Medical Inc., Irvine, Calif.), or an InterLink™ System (Baxter Healthcare Corporation, Deerfield, Ill.) injection port with pre-slit septum in combination with an InterLink™ cannula (Becton Dickinson & Co., Franklin Lake, N.J.). For the purposes of the present invention, the principal requirements for connector arrangement 119 and the valved connector arrangement of injection port 80 are that (i) they are capable of making an airtight connection when they are in engagement with one another, and (ii) the valved connector arrangement of injection port 80 is self-sealing when connector arrangement 119 (and hence the holder containing the bone cement's liquid monomer component) is disconnected from container 10.

Figure 6:
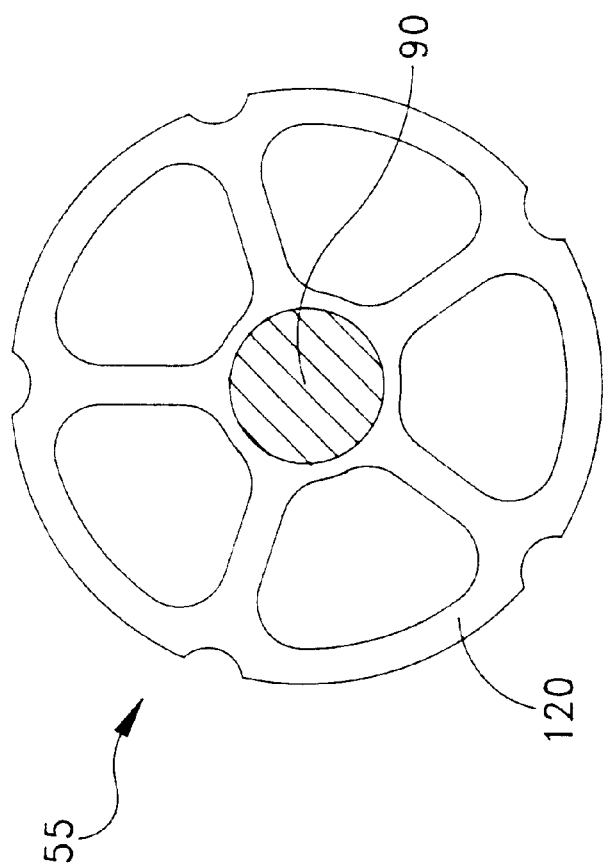
FIG. 6 is a top view, partially in section, of the distal end of the agitator associated with the container shown in FIG. 1.

Looking next at FIGS. 1 and 6, agitator 55 comprises a shaft 90 having a mixing paddle 120 disposed at its distal end and a T-shaped handle 125 disposed at its proximal end. T-shaped handle 125 comprises a pair of lateral extensions 127. Agitator 55 is disposed so that its shaft 90 extends through opening 85 in cap 50 and opening 110 in barrier means 70, whereby the agitator's mixing paddle 120 can be urged to mix the cement components located in the interior of sealed container 10 by means of handle 125. In particular, agitator 55 is arranged so that reciprocal movement of handle 125 relative to container 10 will cause mixing paddle 120 to move in a reciprocal fashion within the interior of container 10.

Vacuum pump 15, vacuum line 20, the one or more check valves 25, vacuum indicator 30, and filter 35 are all preferably of the sort disclosed in pending U.S. patent application Ser. No. 08/577698, filed Dec. 22, 1995 by Kwan-Ho Chan for VACUUM SYSTEM, which application is hereby incorporated herein by reference. Alternatively, vacuum pump 15, vacuum line 20, the one or more check valves 25, vacuum indicator 30, and filter 35 can be generally equivalent elements of the sort well known in the art.

Looking next at FIG. 7, a holder 130 is shown for containing the bone cement's liquid monomer component. Holder 130 comprises an elongated cavity 135 for containing a supply of liquid monomer 140, an egress port 145 terminating in a connector arrangement 119 of the sort described above, and a sliding piston 155. Piston 155 closes off the rear end of elongated cavity 135 and, has its proximal surface 160 exposed to the ambient atmosphere. Piston 155 is adapted to make a close sliding fit with the walls of cavity 135, whereby piston 155 can move distally within cavity 135 as the liquid monomer is withdrawn from the holder, as will hereinafter be discussed in further detail.

System 5 can be used to mix bone cement as follows. First, holder 130 (FIG. 7) is connected to the sealed container's injection port 80. This is done by engaging connector arrangement 119 of monomer holder 130 with the valved connector arrangement of injection port 80 (FIG. 1). Then vacuum line 20 is connected to evacuation port 75. This is done by engaging connector arrangement 118 of vacuum line 20 with the valved connector arrangement of evacuation port 75 (FIG. 1). Then vacuum pump 15 is used to pull a vacuum in container 10, whereby the air present in container 10 will be evacuated from the container, and whereby liquid monomer 140 (FIG. 7) stored in holder 130 will be drawn into container 10 and into contact with the powdered polymer and/or copolymer stored in container 10. Next agitator 55 is used to mix liquid monomer 140 with the powdered polymer and/or copolymer 45 (FIG. 1) so as to form the desired bone cement. The vacuum line 20 may be disconnected from the container's exhaust port 75 before or after mixing. The mixed cement is then ready to be used, either directly in container 10 if the container is the form of a cartridge for a cement dispenser, or by transferring the mixed cement from container 10 into a cartridge for a cement dispenser if container 10 is a simple mixing bowl or other vessel.

Looking next at FIG. 8, another holder 165 is shown for containing the bone cement's liquid monomer component. Holder 165 comprises a collapsible package 170 having an egress port 17 terminating in a connector arrangement 119 of the sort described above. With the arrangement of holder 165, when holder 165 is connected to container 10 and a vacuum is then drawn in container 10, ambient atmospheric pressure will act on collapsible package 170 so as to cause the liquid monomer to pass out of holder 165 and into container 10.

Looking next at FIG. 9, yet another holder 185 is shown for containing the bone cement's liquid monomer component. Holder 185 comprises an injector sleeve 190 which is fit over the distal end of a glass ampoule 195.

Injector sleeve 190 includes an egress port 200 terminating in a connector arrangement 119 of the sort described above. O-rings 205 are disposed in the inside side wall of injector sleeve 190, to make an airtight seal with ampoule 195.

Ampoule 195 has a traditional configuration which includes an easily fractured neck at one end. Ampoule 195 holds the bone cement's liquid monomer component 140. In addition, and quite significantly, ampoule 195 also preferably holds a gas column 210. Gas column 210 is provided to facilitate withdrawal of the monomer component from the fixed volume glass ampoule vessel by vacuum. In fact, when ampoule 195 is in communication with container 10 and a vacuum is thereafter drawn in that container gas column 210 will effectively expand in the ampoule as the vacuum is drawn in the container until the pressure of gas column 210 in ampoule 195 equilibrates with the level of the vacuum in container 10. Thus, the expanding gas column 210 effectively expels monomer 140 from ampoule 195 and into container 10 as a vacuum is established in container 10.

The minimum volume of gas required to completely expel monomer 140 from ampoule 195 under the influence of the vacuum in container 10 is governed by Boyle's Law, as follows:

$$V_O \times P_O = (V_M + V_O) \times P_C$$

where:
- $V_O$=volume of gas in ampoule 195
- $P_O$=pressure of gas in ampoule 195
- $V_M$=volume of monomer in ampoule 195
- $P_C$=vacuum level in container 10 (assumed to be constant).

By way of example, suppose the volume of monomer in ampoule 195 (i.e., $V_M$) is 40 cc, the pressure of gas in ampoule 195 (i.e., $P_O$) is 30 mm Hg, the ambient atmospheric pressure is 30 mm Hg, the vacuum in container 10 (i.e., Pc) is 22 mm HG below ambient atmospheric pressure (i.e., 30 mm HG–22 mm HG=8 mm HG), then $$V_O \times 30 = (40 + V_O) \times 8$$

or $$V_O = 14.5 \text{ cc}$$

In practice, since the surface tension of monomer 140 is very low, the monomer will tend to flow out of ampoule 195 under the influence of gravity alone. In other words, the monomer will flow out of ampoule 195 even if the minimum volume of gas required to completely expel monomer 140 from ampoule 195 is not met. Monomer 40 will, of course, flow out of ampoule 195 much better when the volume and pressure requirement are met. And, as might be expected, the system will work best if gas column 210 is sealed in ampoule 195 under pressure.

In use, the easily fractured neck of ampoule 195 is broken off by snapping it along a prescored line which is provided for this purpose. This effectively opens ampoule 195. Next injector sleeve 190 is slipped over the open end of glass ampoule 195. O-rings 205 seal vessel 195 within injector sleeve 190. On account of this construction, when holder 185 is connected to container 10 and a vacuum is then drawn in container 10, the gas column 210 disposed above liquid monomer 140 will expand so that the liquid monomer-will flow out of the holder and into container 10. In this respect it is also to be appreciated that, when holder 185 is connected up to container 10 and a vacuum is then drawn in container 10, atmospheric pressure acting on the top surface 22 of glass ampoule 195 will urge the ampoule further down into injector sleeve 190, if the ampoule is not already maximally advanced into the injector sleeve.

Figure 10:
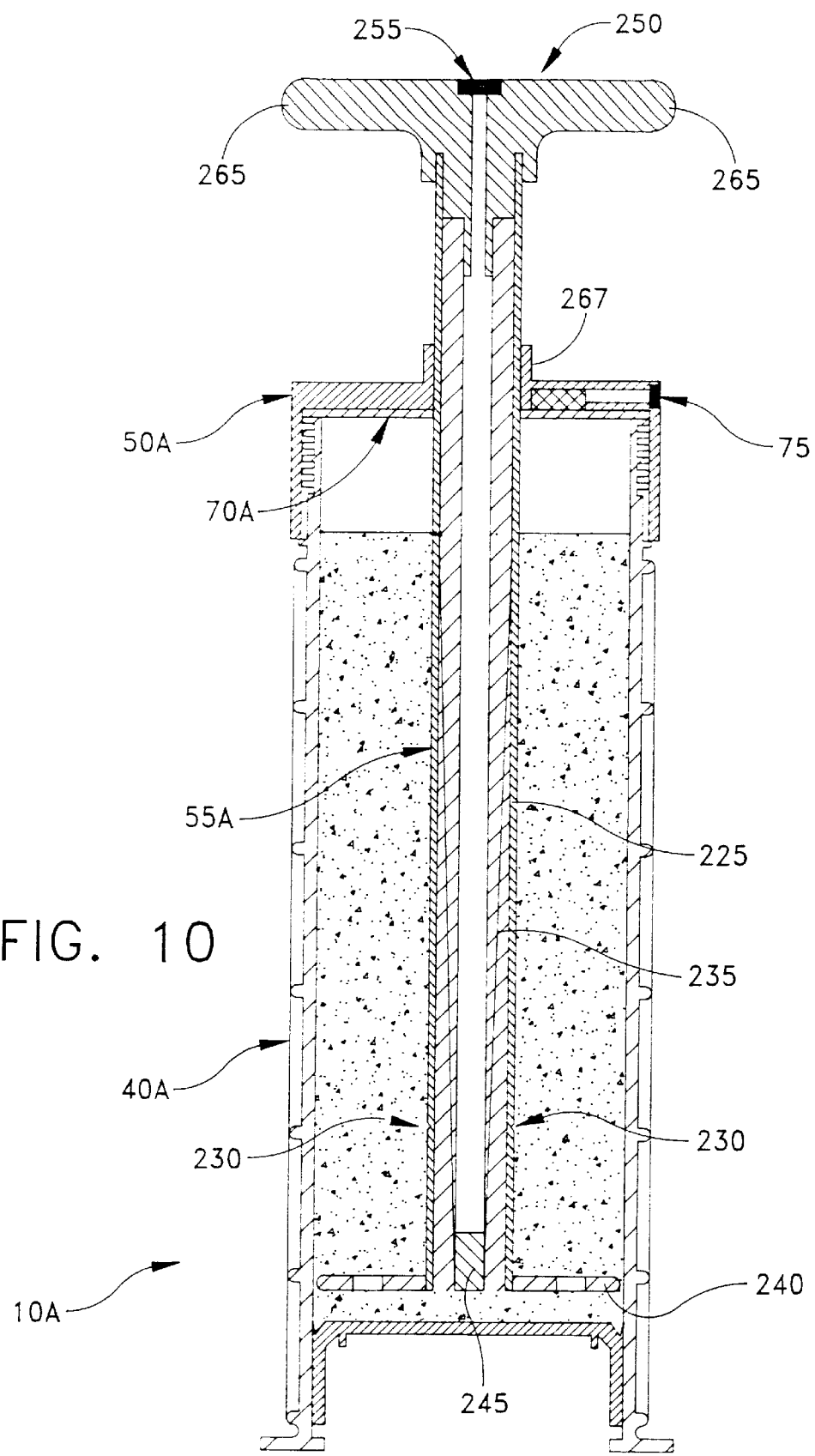
FIG. 10 is a side view in section of an alternative form container which can be used in conjunction with the system shown in FIG. 1.
Figure 11:
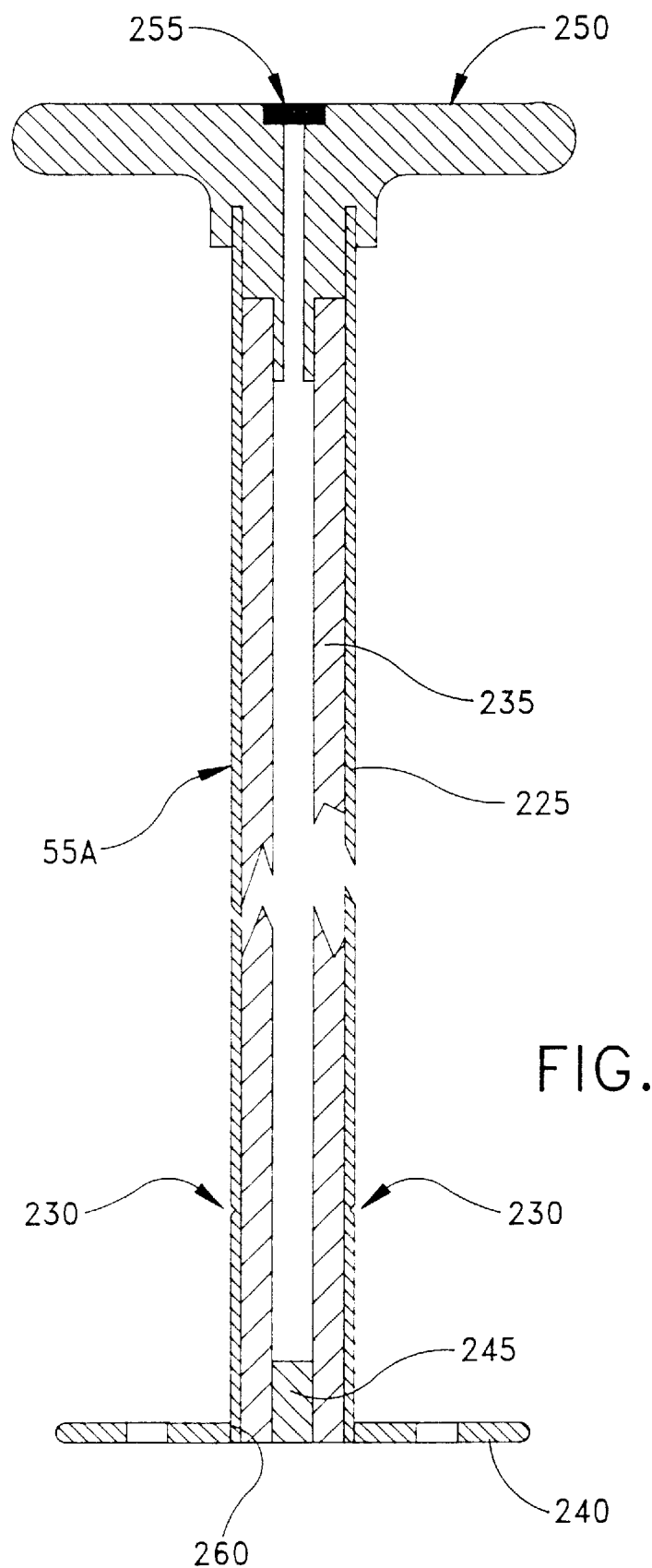
FIG. 11 is a side view in section of the agitator associated with the container shown in FIG. 10.
Figure 12:
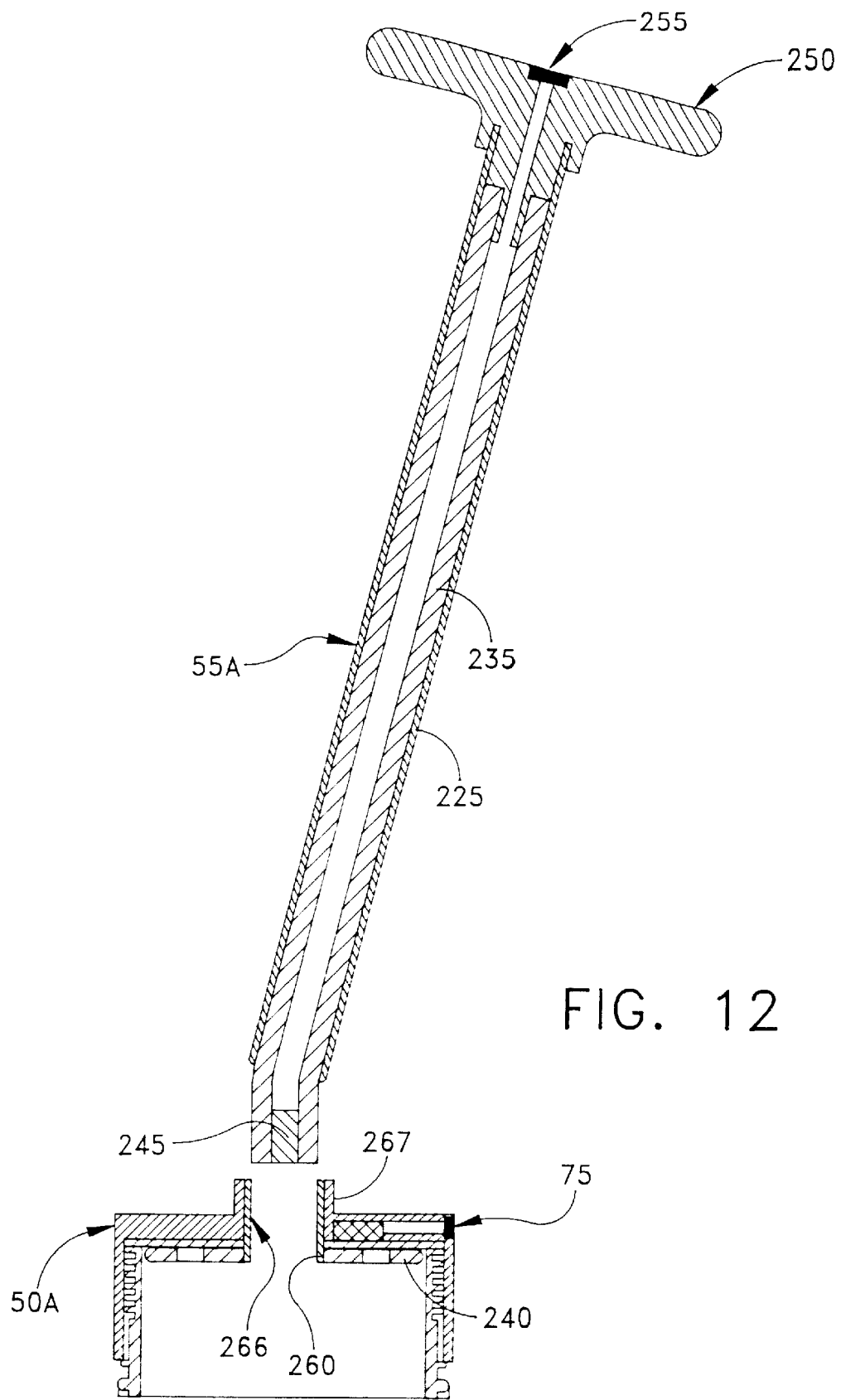
FIG. 12 is a side view in section showing the distal end of the agitator's thin-walled exterior tube being broken off, and the agitator's resilient interior tube withdrawing the porous plug, whereby the remaining stub of the thin-walled exterior tube can become an ejection port for the sealed container.

Looking next at FIGS. 10–12, an alternative container 10A is disclosed which can be used in place of the container 10 in system 5. Container 10A is identical to the container 10 previously disclosed, except as will hereinafter be discussed.

First, container 10A is generally intended to comprise a container body 40A which is in the form of a cartridge for a cement dispenser. Container body 40A is generally not intended to be in the form of a sealed mixing bowl or other non-cartridge vessel, as might be the case with the container body 40 previously disclosed. Of course, it should also be appreciated that nothing in the present invention requires that container body 40A be in the form of a cartridge for a cement dispenser; it is merely anticipated that this will be the most useful form for container body 40A.

Second, container 10A has a cap 50A which is identical to the cap 50 previously disclosed, except that cap 50A omits the injection port 80 previously disclosed in connection with container 10. Furthermore, if desired, the indirect pathways of container 10 (constituted by the surface grooves 105 formed in the cap's bottom surface and by the radial slits 115 formed in barrier means 70) may be omitted in container 10A. In such a case, alternative barrier means 70A may be provided, wherein such barrier means 70A are formed out of a porous or semi-porous material such that barrier means 70A can serve to minimize any undesired materials (e.g., powdered polymer and/or copolymer, liquid monomer, and/or mixed cement) from passing into the container's exhaust port 75, while still permitting gas to be evacuated from container 10A through exhaust port 75.

Third, container 10A includes an agitator 55A which differs significantly from the agitator 55 previously disclosed in connection with container 10. Agitator 55A comprises a thin-walled exterior tube 225 having a breakaway notch 230 (FIGS. 10 and 11) formed near its distal end, a resilient interior tube 235 disposed inside the thin-walled exterior tube 225, a perforated disk 240 disposed at the distal end of thin-walled exterior tube 225 and resilient interior tube 235, a porous plug 245 closing off the distal end of resilient interior tube 235, a T-shaped handle 250 connected to the top ends of thin-walled exterior tube 225 and resilient interior tube 235, and an injection port 255 formed in handle 250.

Thin-walled exterior tube 225 is formed out of breakable plastic, e.g., polyethylene. Breakaway notch 230 is formed near the distal end of thin-walled exterior tube 225, and preferably comprises a peripheral groove formed in the outer surface of the tube. Breakaway notch 230 permits thin-walled exterior tube 225 to be broken off in a snapping action, as will hereinafter be discussed in further detail.

Resilient interior tube 235 is disposed within thin-walled exterior tube 225. Interior tube 235 is formed out of a resilient material which will flex but remain intact when thin-walled exterior tube 225 is broken off at its breakaway notch 230 in a snapping motion. At the same time, however, interior tube 235 is formed out of a material which is sufficiently rigid in an axial direction such that porous plug 245 will remain securely in place within agitator 55A when the agitator is used to mix bone cement within container 10A, as will hereinafter be discussed in further detail. Resilient interior tube 235 is preferably formed out of plasticized polyvinylchloride (PVC) or silicone.

Perforated disk 240 is identical to the perforated disk 120 described above in connection with agitator 55, except that perforated disk 240 includes an opening 260 (FIGS. 11 and 12) at its center. Opening 260 in perforated disk 240 receives, and is joined to, the distal end of thin-walled exterior tube 225 (FIGS. 10 and 11), whereby the thin-walled exterior tube 225 can be used to move perforated disk 240 distally and proximally within container 10A so as to mix the contents of container 10A. As such mixing occurs, the distal end of resilient interior tube 235 and porous plug 245 will be exposed to the contents of container 10A (FIGS. 10 and 11).

Porous plug 245 closes off, and is securely fastened to, the distal end of resilient inner tube 235. Porous plug 245 is formed so that it will prevent powdered polymer and/or copolymer material from getting into the central passageway of resilient inner tube 235, yet still permit air and liquid monomer to pass through the plug. In this way, the creation of a vacuum within the body of container 10A can be used to draw liquid monomer downward from injection port 255, whereby the liquid monomer will pass down the length of resilient interior tube 235, through porous plug 245 and then enter the interior of container 10A.

Handle 250 is secured to both thin-walled exterior tube 225 and resilient interior tube 235. As a result, handle 250 can be used to move the agitator's perforated disk 240 in a reciprocal motion within the interior of container 10A, yet can also be used to withdraw resilient interior tube 235 and porous plug 245 from container 10A once the thin-walled exterior tube 225 has been snapped off along its breakaway notch 230, as will hereinafter be discussed in further detail. Handle 250 preferably comprises a pair of lateral extensions 265 (FIG. 10).

Injection port 255 is formed in handle 250. Injection port 255 comprises a valved opening for introducing liquid monomer into the interior passageway of resilient interior tube 235. To this end, injection port 255 comprises a valved connector arrangement of the sort adapted to form an airtight seal with its counterpart connector arrangement 119 formed on a monomer holder, e.g. a holder such as holder 130 (FIG. 7), holder 165 (FIG. 8) and/or holder 185 (FIG. 9). In particular, injection port 255 in container 10A can be substantially the same as the injection port 80 disclosed in connection with container 10 except, of course, for the fact that injection port 255 is formed in handle 250 and provides an entryway to the interior of resilient interior tube 235, whereas the injection port 80 associated with container 10 is disposed in that container's cap 50 and opens directly on the interior of that container.

It is to be noted that the sealed container 10A is pre-filled with an appropriate supply of the bone cement's powdered polymer and/or copolymer component.

Container 10A is intended to be used with system 5 as follows. First, a monomer holder (e.g., a monomer holder 130 as shown in FIG. 7, or a monomer holder 165 as shown in FIG. 8, or a monomer holder 185 as shown in FIG. 9, or some other such holder) is connected to the injection port 255 formed in handle 250. This is done by engaging connector arrangement 119 of the monomer holder with the valved connector arrangement of injection port 255 so as to establish an airtight connection. Then vacuum line 20 is connected to the container's evacuation port 75. This is done by engaging connector arrangement 118 (FIG. 1) of vacuum line 20 with the valved connector arrangement of evacuation port 75 so as to establish an airtight connection. Next, a vacuum is pulled in container 10A using vacuum pump 15. This vacuum draws the bone cement's liquid monomer component out of its holder and down the interior passageway of resilient interior tube 235, whereupon the liquid monomer component passes through porous plug 245 and enters the interior of container 10A to join the bone cement's powdered polymer and/or copolymer component. Then the monomer holder is disconnected from injection port 255, and agitator 55A is used to mix the cement in container 10A by moving perforated disk 240 back and forth within the container. Next, vacuum line 20 is disconnected from container 10A, and agitator 55A is retracted relative to container 10A (i.e., agitator 55A is moved so that its perforated disk 240 resides adjacent to barrier means 70 or 70A, depending on which type of barrier means may be provided). Then the proximal end of thin-walled exterior tube 225 is snapped off at breakaway notch 230 so as to provide a stub 266 (FIG. 12), and the proximal end of agitator 55A is withdrawn from container 10A, carrying resilient interior tube 235 and porous plug 245 away from the container 10A. This leaves hollow stub 266 clear and the container 10A ready to be loaded into a cement dispenser of the sort well known in the art, whereupon the mixed cement within container 10A can be dispensed out the hollow stub 266. Preferably breakaway notch 230 on the thin-walled exterior tube 225 is positioned such that stub 265 will lie substantially flush with a cap projection 267 (FIGS. 10 and 12) after the proximal end of agitator 55A is removed from container 10A, whereby various nozzle fixtures can be easily mounted to cap projection 267 so as to facilitate dispensing of bone cement.

Figures 13, 14:
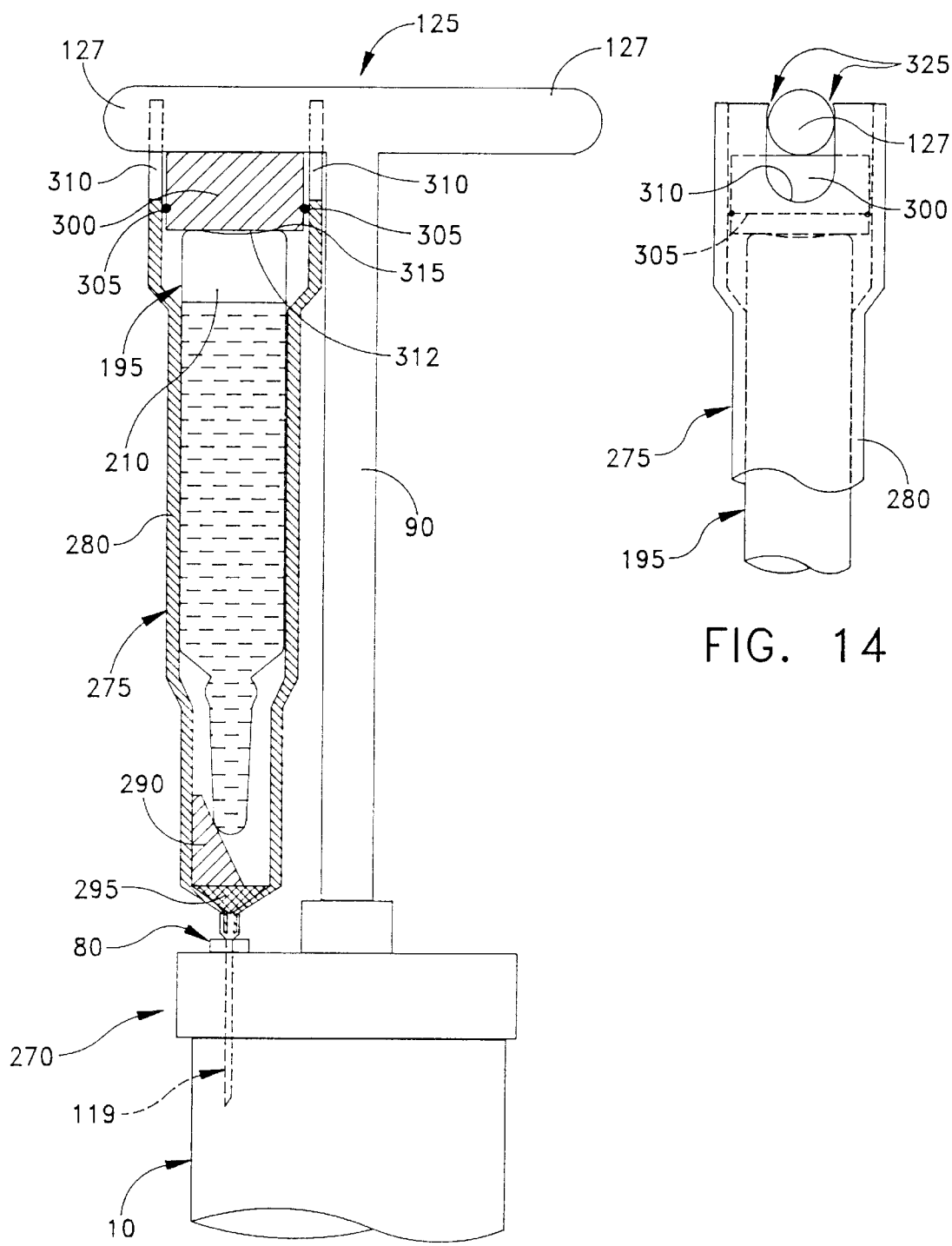
FIG. 13 is a side view in section showing the ampoule breaker/injector device connected to the injection port of a container.
FIG. 14 is a partial side view of the proximal end of the ampoule breaker/injector device shown in FIG. 13, except that the view of FIG. 14 has been taken at a 90 degree angle to the view of FIG. 13.
Figure 15:
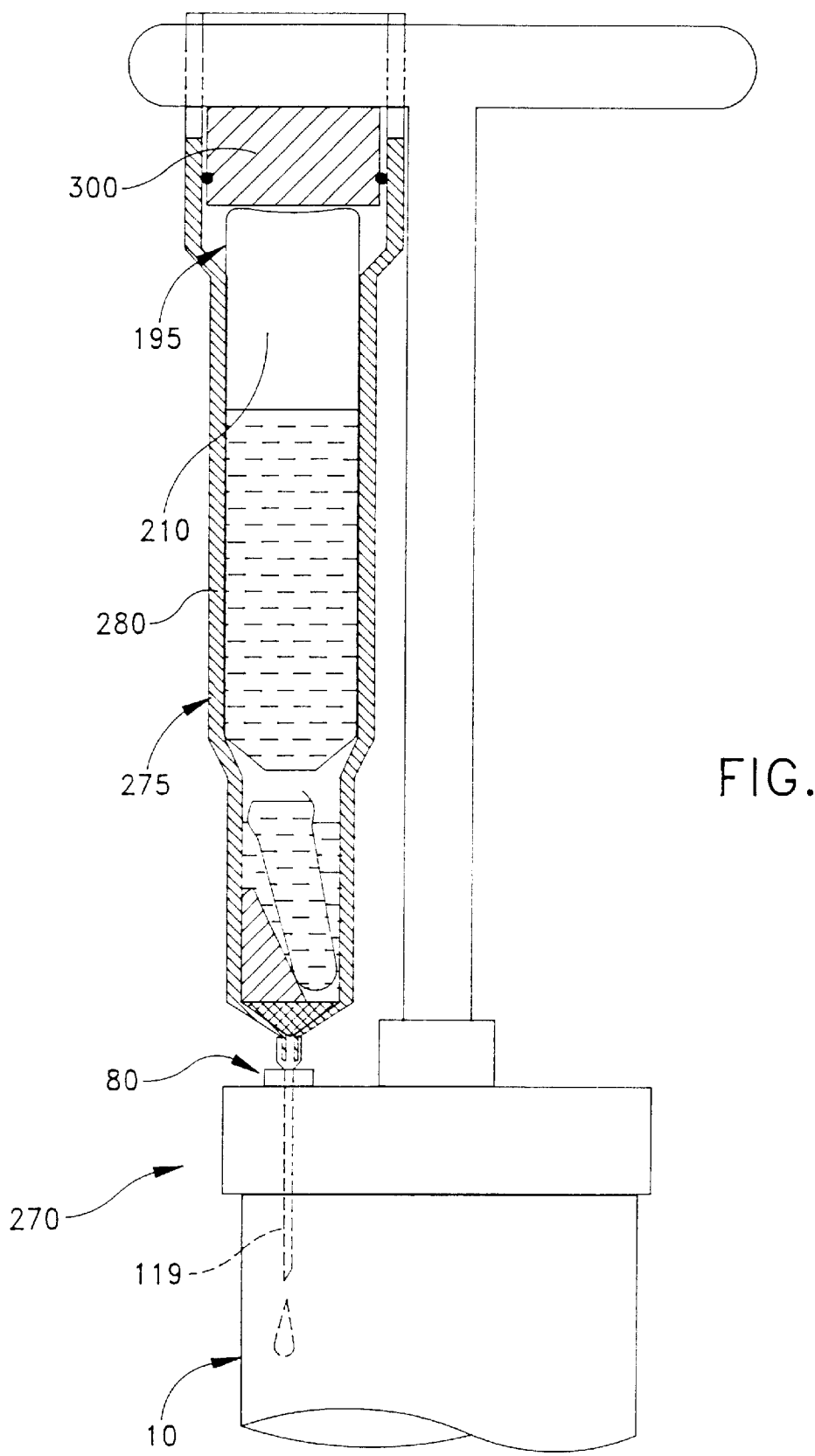
FIG. 15 is a side view in section like that of FIG. 13, except that the glass ampoule storing the bone cement's liquid monomer component is shown moved distally within the ampoule breaker/injector device, with the distal end of the ampoule having broken off to release the liquid monomer.

Looking next at FIGS. 13–15, another container arrangement 270 is shown which can be used with system 5.

Container arrangement 270 comprises a container 10 of the sort previously described and shown in FIGS. 1–6, and an ampoule breaker/injector 275 which is connected to the container's injection port 80. Ampoule breaker/injector 275 is arranged so that it will automatically (i) break a glass ampoule 195 of the sort shown in FIGS. 9 and 13 when a vacuum is established in container 10, and (ii) direct the released monomer liquid into the container's injection port 80. More particularly, ampoule breaker/injector 275 acts as a caddy for the ampoule 195 until a vacuum is to be drawn in container 10 and the liquid monomer in the ampoule is to be used, at which time ampoule breaker/injector 275 facilitates release of the liquid monomer from the ampoule, and then directs the liquid monomer through the container's injection port 80 and into contact with powdered polymer and/or copolymer powder previously packaged in the sealed container 10. The volume of the gas column used to efficiently expel the liquid monomer from the ampoule is as previously described in connection with the arrangement shown in FIG. 9.

Ampoule breaker/injector 275 comprises an elongated body 280, a connector arrangement 119 disposed at the distal end of body 280, an internal wedge 290 set near the distal end of body 280, a glass trap 295 disposed between wedge 290 and connector arrangement 119, and a proximal piston 300 having an associated O-ring 305. A U-shaped groove 310 is formed in the proximal end of body 280, as will hereinafter be disclosed in further detail.

Elongated body 280 is adapted to support glass ampoule 195 so that it is axially aligned with container 10, and so that the ampoule can make a sliding fit within the interior of elongated body 280.

Connector arrangement 119 is disposed at the distal end of elongated body 280. Connector arrangement 119 is in fluid communication with the interior of elongated body 280. As discussed above, connector arrangement 119 is of the sort adapted to form an airtight seal with the valved connector arrangement of injection port 80, as also discussed above.

Internal wedge 290 is set near the distal end of elongated body 280. Wedge 290 is fixed to the internal side wall of elongated body 280. Wedge 290 is set at an angle to the longitudinal axis of the elongated body, whereby the leading tip of a glass ampoule 195 located within elongated body 280 will break off when that ampoule is driven distally against wedge 290. In essence, wedge 290 translates the distal movement of glass ampoule 195 into the lateral movement used to break off the leading tip of the ampoule and release its liquid monomer.

Glass trap 295 is disposed within elongated body 280, between internal wedge 290 and connector arrangement 119. Glass trap 295 permits liquid monomer (released by the broken ampoule 195) to pass through to connector arrangement 119, whereupon the liquid monomer will enter the interior of container 10; at the same time, however, glass trap 295 prevents glass chards from the broken ampoule from reaching the bone cement's powder polymer and/or copolymer component which is disposed in container 10.

Piston 300 is disposed in the proximal end of elongated body 280, so that the piston's O-ring 305 is positioned on the distal side of U-shaped groove 310. The piston's associated O-ring 305 forms an airtight seal with the interior wall of elongated body 280. The distal end surface 312 (FIG. 13) of piston 300 contacts the proximal end surface 315 of ampoule 195. The O-ring 305 is disposed distal to the lowest point of the U-shaped groove 310.

As a result of the foregoing construction, when a vacuum is drawn within container 10 using vacuum pump 15, this vacuum will extend up into the interior of elongated body 280, thereby urging piston 300 to travel distally within elongated body 280. The moving piston 300 in turn drives ampoule 195 distally, so that the leading nose of the glass ampoule is driven against internal wedge 290, thereby breaking off at the prescored neck of the ampoule and releasing the liquid monomer contained in the ampoule. This liquid monomer is then drawn down into container 10 by the same vacuum, whereby the monomer will mix with the powdered polymer and/or copolymer previously packed into container 10. Preferably ampoule 195 includes the gas column 210 previously discussed.

Preferably, piston 300 has an enlarged cross-section relative to ampoule 195, as shown in FIGS. 13–15, so as to generate greater driving force on the top end of the ampoule.

U-shaped groove 310 is formed at the proximal end of elongated body 280 (FIGS. 13 and 14). Groove 310 is sized so as to accept one of the lateral extensions 127 of handle 125. Preferably the top end of groove 310 is narrowed slightly as shown at 325 (FIG. 14) so as to releasably hold a lateral handle extension 127 in groove 310. The positioning of a lateral handle extension 127 in groove 310 serves to stabilize the proximal end of elongated body 280 relative to agitator shaft 90. Furthermore, since the agitator's handle 125 will tend to be drawn downward as a vacuum is drawn in container 10, groove 310 provides a guide for one of the distally-moving lateral handle extensions 127. Additionally, since groove 310 permits one of the lateral handle extensions 127 to remain in engagement with the top of the distally-moving piston 300, the force generated by the moving lateral handle extension 127 will combine with the force generated by the moving piston 300 so as to assist in the breakage of glass ampoule 195. Furthermore, in the event that the vacuum created in container 10 is unable to drive piston 300 distally with sufficient force to break the glass neck of the ampoule, the presence of groove 310 permits the user to manually depress handle 125 so as to increase the distal pressure applied to the ampoule, whereby ampoule 195 can be broken.

The container arrangement shown in FIGS. 13–15 is intended to be used as follows. First ampoule breaker/injector 275 is connected to the container's injection port 80. This is done by engaging connector arrangement 119 of ampoule breaker/injector 275 with the valved connector arrangement of injection port 80. Then an ampoule 195 is loaded into the interior of elongated body 280. Next piston 300 is set atop ampoule 195. Then one of the lateral extensions 127 of handle 125 is set in U-shaped groove 310, so that the lateral extension contacts the top surface of piston 300. Next vacuum line 20 is connected to exhaust port 75 on container 10 (not shown in FIGS. 13–15, but shown in FIGS. 1 and 2). This is done by engaging connector arrangement 118 of vacuum line 20 with the valved connector arrangement of exhaust port 75. Then a vacuum is pulled in container 10, using vacuum pump 15. Creation of a vacuum within the interior of container 10 causes piston 300 to move distally within elongated body 280, driving the distal end of ampoule 195 against internal wedge 290. At the same time, creation of a vacuum within container 10 causes agitator 55 to move distally, whereupon the lateral extension 127 of handle 125 disposed in groove 310 will bring additional distally-directed force to bear on the proximal end of piston 300. Additionally, further downward force can be applied to the proximal end of ampoule 195 by manually pressing down on handle 125 if necessary. As a result of the foregoing, the distal end of ampoule 195 will be driven against internal wedge 290 so that the ampoule's glass neck will be broken off, thereby releasing the liquid monomer contained in ampoule 195 (FIG. 15). This monomer liquid will then pass down into the interior of container 10, where it will come into contact with the bone cement's powdered polymer and/or copolymer component which was previously packaged in the sealed container. Then ampoule breaker/injector 275 is dismounted from container 10 and the liquid and solid cement components disposed in container 10 are mixed together using agitator 55. Finally vacuum line 20 is disconnected from the container's exhaust port 75. The mixed cement is then ready to be used, either directly in container 10 if container 10 is in the form of a cartridge for a cement dispenser, or by thereafter transferring the mixed cement from container 10 into a cartridge for a cement dispenser if the container 10 is a simple mixing bowl or other non-cartridge vessel.

Figure 16:
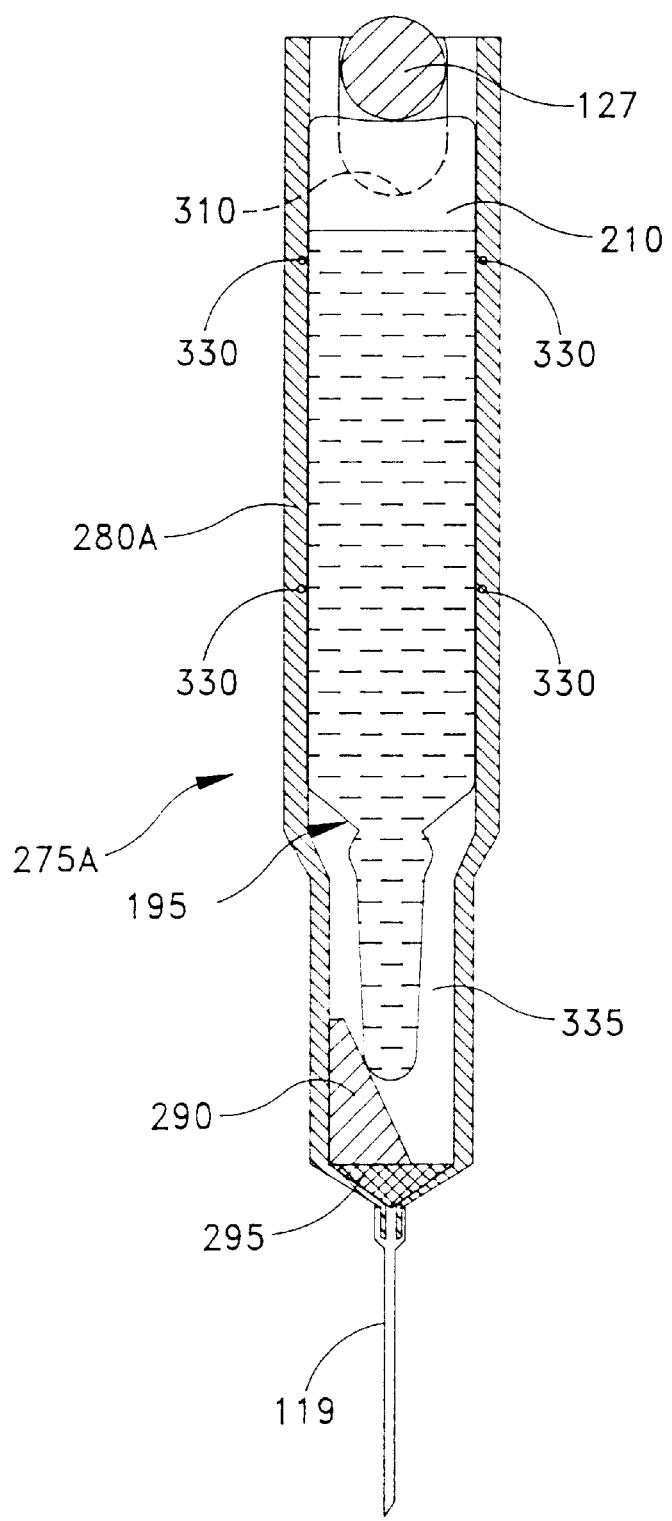
FIG. 16 is a side view in section showing an alternative form of ampoule breaker/injector device.

Looking next at FIG. 16, an alternative form of ampoule breaker/injector 275A is shown. Ampoule breaker/injector 275A is similar to the ampoule breaker/injector 275 previously disclosed, except that the proximal end of elongated body 280A does not have an enlarged cross-section relative to the middle portion of the elongated body, and piston 300 has been replaced by one or more O-rings 330 mounted in annular grooves formed in the side wall of elongated body 275A. O-rings 330 make a close sliding fit with the outsidewall of glass ampoule 195. O-rings 330 are disposed distal to the lowest point of the U-shaped groove 310. With the arrangement shown in FIG. 16, application of a vacuum to connector arrangement 119 will create a vacuum within the space 335 in the assembly, thereby causing ampoule 195 to move distally against wedge 290 so as to break the leading neck of the glass ampoule and thereby release the monomer fluid held therein.

Modifications of the Preferred Embodiments

It is, of course, possible to modify the preferred embodiments disclosed above without departing from the scope of the present invention.

Thus, for example, one could substitute a plurality of perforated holes for the radial slits formed in barrier means 70.

Or one could substitute a rotary-type agitator for the reciprocal-type agitator disclosed above. With such an alternative arrangement, the agitator's paddle element would move circumferentially about the perimeter of the container, rather than back and forth along its length.

Furthermore, one could use another type of barrier means with the container 10 shown in FIGS. 13–15, e.g., one could use the porous or semi-porous barrier means 70A previously discussed in the context of container 10A.

Also, ampoule breaker/injector 275 or ampoule breaker/injector 275A could be used with container 10A if desired, in which case the monomer would be injected into the handle of the agitator.

Still other modifications will be obvious to a person skilled in the art, and are considered to fall within the scope of the present invention.

Advantages of the Invention

Significant advantages are achieved through the use of the present invention.

For one thing, the present invention provides an improved system for mixing bone cement.

For another thing, the present invention provides a more convenient system for mixing bone cement in a vacuum in an operating room environment.

And the present invention provides an improved method for mixing bone cement.

Additionally, the present invention provides a more convenient method for mixing bone cement in a vacuum in an operating room environment.

What is claimed is:

1. Apparatus comprising:

a substantially rigid vessel defining an interior region;

a frangible neck formed on said vessel and communicating with said interior region of said vessel;

a selected quantity of a liquid bone cement disposed in said interior region of said vessel;

a gas column disposed in said interior region of said vessel;

an injector element for receiving the neck of said vessel and at least a portion of the remainder of said vessel, and said injector device including an egress port; and a sealing element disposed between said injector element and said at least a portion of the remainder of said vessel, said sealing element forming an airtight seal therebetween;

wherein said gas column expands to expel said liquid bone cement from said vessel into said egress port as a vacuum is drawn in a container connected to said egress port.

* * * * *